United States Patent [19]

Magdassi et al.

[11] Patent Number: 5,785,969
[45] Date of Patent: Jul. 28, 1998

[54] METHOD AND PHARMACEUTICAL AND DIAGNOSIS COMPOSITIONS FOR DRUG TARGETING

[75] Inventors: Shlomo Magdassi; Zichria Zazkay Rones, both of Jerusalem; Ofer Toledano, Tel Aviv, all of Israel

[73] Assignee: Yissum, Research Development Company of The Hebrew University of Jerusalem, Jerusalem, Israel

[21] Appl. No.: 600,988

[22] PCT Filed: Aug. 25, 1994

[86] PCT No.: PCT/EP94/02827

§ 371 Date: Jul. 22, 1996

§ 102(e) Date: Jul. 22, 1996

[87] PCT Pub. No.: WO95/06483

PCT Pub. Date: Mar. 9, 1995

[30] Foreign Application Priority Data

Sep. 2, 1993 [IL] Israel ............................................ 106887

[51] Int. Cl.$^6$ .......................... A61K 39/395; A61K 47/44
[52] U.S. Cl. ................................... 424/181.1; 424/178.1; 424/283.1; 424/502; 514/943; 436/547
[58] Field of Search .......................... 424/178.1, 181.1, 424/283.1, 450, 502; 514/2, 789, 943; 436/547

[56] References Cited

U.S. PATENT DOCUMENTS 4,957,735  9/1990  Huang .................................. 424/85.8
5,135,736  8/1992  Anderson et al. ........................ 424/1.1

OTHER PUBLICATIONS

Chekhonin et al., Fatty acid acylated Fab–fragments of antibodies to neurospecific proteins as carriers for neuroleptid targeted delivery in brain. FEBS Letters 287 (1,2):149–152, 1991.

Huang et al., Monoclonal Antibody Covalently Coupled with Fatty Acid. Journal of Biological Chemistry 255:8015–8018, 1980.

Primary Examiner—Marian C. Knode
Assistant Examiner—Donna C. Wortman
Attorney, Agent, or Firm—Birch, Stewart, Kolasch & Birch, LLP

[57] ABSTRACT

The new pharmaceutical and diagnostic compositions comprise antibody-aggregates and hydrophobic drug or marker molecules. The drug or marker molecules are solubilized inside micelle-like antibody-aggregates. In a process for preparing such types of compositions, hydrophobic residues are attached to the antibodies in the presence of a surface active agent. After removal of this agent the hydrophobic drug or marker molecules are solubilized inside the resulting antibody aggregates. A method for targeting molecules towards specific cells and sites within a living body is also disclosed.

10 Claims, 3 Drawing Sheets

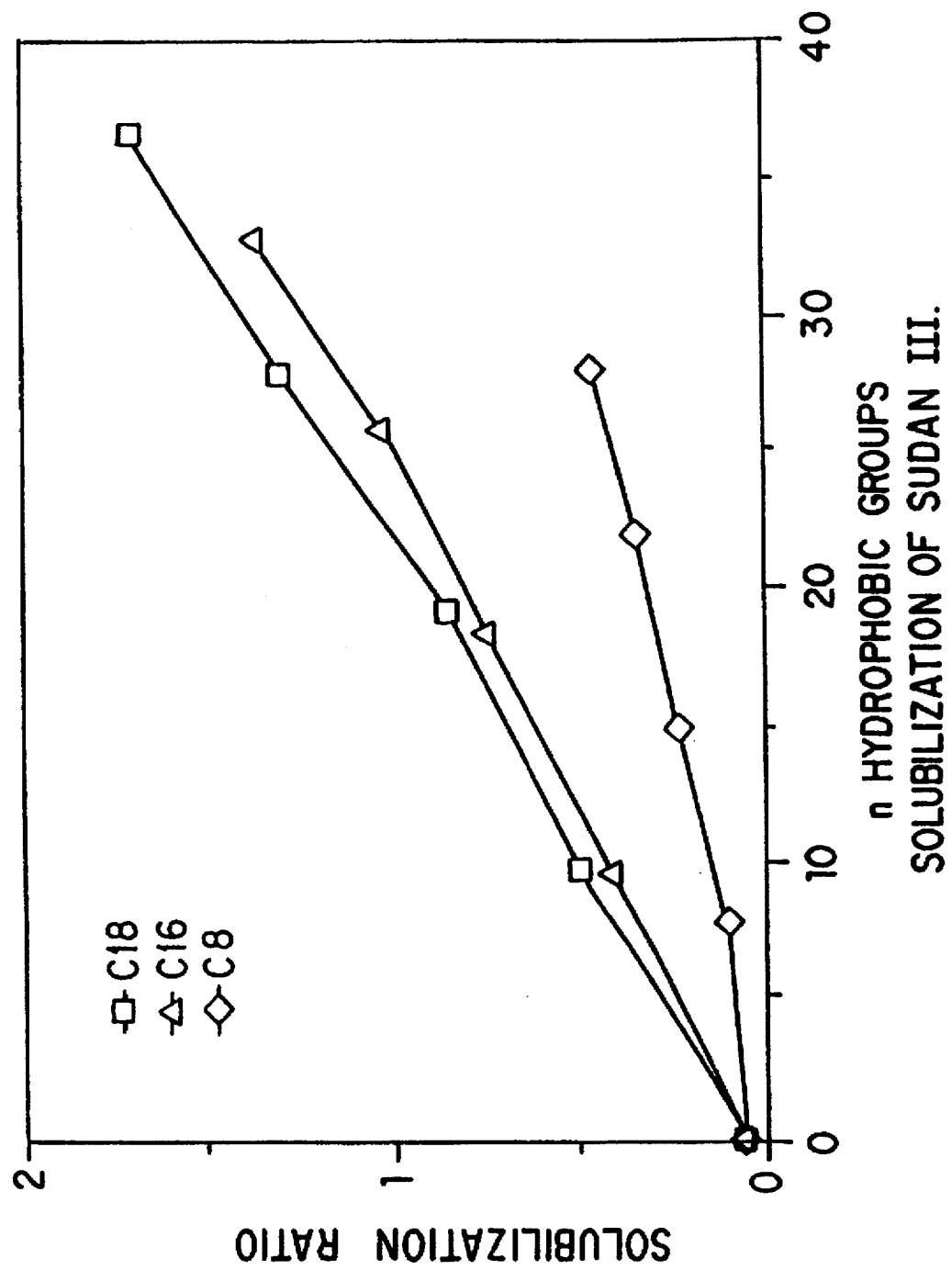

METHOD AND PHARMACEUTICAL AND DIAGNOSIS COMPOSITIONS FOR DRUG TARGETING

This application is a 371 of PCT/EP94/02827, filed Aug. 25, 1994.

The present invention relates to pharmaceutical and diagnostic compositions containing antibody aggregates and a drug or a marker and a method for drug targeting and diagnostics. More specifically said invention relates to a composition containing aggregates of antibodies, wherein a drug or any other marker probe is solubilized in said aggregates. The invention relates also to a process for the preparation of said pharmaceutical and diagnostic composition and to the method of targeting the aggregates to specific molecules or sites in the body, or in vitro tests.

Since the aggregates are composed of antibodies, they are capable of recognizing specific molecules, and therefore can be used for drug targeting or diagnostic purposes, provided that suitable molecules—drugs, fluorescent markers, etc.—can be loaded into these aggregates.

BACKGROUND OF THE INVENTION

The present invention relates to drug targeting, or marker molecule targeting, by small antibody aggregates, while the targeting molecules also form the carrier for specific targeted molecule. The advantages of being able to direct a drug to the tissue or cells where it is required, and to minimize the amount delivered to inappropriate sites has implications for many clinical situations, such as cancer chemotherapy, inflammations and viral infections (Davis S. S et al. Drug Exptl. Clin. Res. 9 632 1985).

In the past, several attempts to achieve drug targeting were reported, by using polyclonal and monoclonal antibodies. These attempts include:

1. Direct chemical attachment of drug molecules to an antibody molecule.
2. Chemical attachment of drugs to antibodies through use of a linkage polymer molecule such as dextran.
3. Attachment of small antibodies to small biodegradable polymeric particles, by covalent linkage by direct adsorption or by adsorption via protein A.
4. Coupling of liposomes with monoclonal antibodies via hydrophobic modification of the antibody.

The above suggested methods of drug targeting have many disadvantages:

a. Covalent attachment of drug molecules require development of a chemical binding process for each drug to be tested.
b. Direct attachment to the antibody may reduce its biological activity.
c. Only a limited amount of drug molecules may be bound, depending on the reaction between the drug and the antibody.
d. The clinical effects of the drugs may be altered upon chemical attachment.
e. Possible leakage of drugs if liposomes are used.
f. Desorption of the antibodies may occur if it is physically adsorbed to a solid particle.
g. Attachment of antibodies to various nanoparticles may not be sufficient to overcome problems related to size of particles, and therefore destruction or clearance of the particles from the body.

The present invention will provide a novel drug targeting method, which overcomes most of the above disadvantages, by the use of antibody aggregates. The antibody-aggregates can also be used for diagnostic purposes, namely detection of specific antigens, in vivo and in vitro tests. This can be achieved by solubilizing various probes in the aggregates, such as hydrophobic fluorescent molecules, or radioactive molecules.

BRIEF DESCRIPTION OF THE INVENTION

The present invention relates to pharmaceutical and diagnostic compositions containing an antibody-aggregates and a drug or a marker wherein the antibody-aggregates are capable of solubilizing hydrophobic molecules, and the drug or the marker probe are solubilized in the aggregates.

The present invention further relates to a process for the preparation of pharmaceutical and diagnostic compositions comprising:

a. Attachment of hydrophobic chains to the antibody molecule, in presence of a surface-active agent. Various chain lengths and degree of modifications are possible.
b. Purification and removal of the surfactant. At this stage the requested aggregates are formed.
c. Solubilization of the required molecule in the aggregate solution.

The present invention also relates to a method for drug targeting towards specific sites in the body (such as antigenic determinants), comprising administration of an effective amount of pharmaceutical to a host. The present invention also relates to a method for in vivo and in vitro diagnostics, in which the aggregates contain molecules which can be detected by suitable instruments.

DESCRIPTION OF THE INVENTION

The new method for drug targeting is based on formation of aggregates of antibodies. These aggregates are formed by covalent attachment of hydrophobic chains to various antibodies, hence leading to micelle-like structures in a similar way to that in which classical surfactant ("detergents") may form micelles. These antibody aggregates have unique properties, especially two: (1) the aggregates are capable of solubilizing hydrophobic molecules, (2) the antibodies may recognize specific antigens. Therefore, such aggregates can be used for drug targeting, while the targeting molecules (the antibodies) also play the role of a conventional carrier. The aggregates are very small—about 200–1000 Å in diameter, hence they might overcome problems which are encountered while using drug carriers based on polymers, emulsions, etc.

It is therefore expected that it would also be possible to solubilize hydrophobic drug molecules in these aggregates. It should be emphasized that the solubilization process is spontaneous, thus there is no need for chemical attachment of the drug to the carrier or to the targeting molecules. The amount of drug which can be solubilized obviously depends on various parameters, such as the molecular structure of the drug, the number and type of the hydrophobic chains, which are chemically linked to the antibody. Clearly, it is required to retain the recognition ability of the antibody for specific antigens. So far we were able to modify the antibodies in a way which did not affect the biological activity (against Herpes virus infected cells, which were used as our testing model).

As already proved for a model system, once the antibodies recognize the specific antigen on the cell surface, the whole aggregates will be attached to the infected cell via the antibody-antigen complex, as presented in FIG. 1. Once the aggregate is attached to the cell or an antigen, a local high concentration of the drug or marker will be obtained in the vicinity of the infected cells, yielding targeting to specific cells only.

This method can be applied either topically (for example, Herpes in the eye), or intravenously due to the small size of the whole carrier.

The process for obtaining the required aggregates is very simple and may be applied rapidly to various types of drugs, probe molecules, and antibodies. The main advantages of the proposed method are:

1. The process is very versatile and is based on a modular approach, which may be adopted by the final user, provided that the drug or probe molecule can be solubilized in the aggregates.
2. It is possible to use various types of hydrophobic chains for preparation of the aggregates to meet the requirement of solubilization of specific molecules.
3. The solubilized molecules are not subjected to any chemical modification: the original molecule is maintained through the whole process.
4. Due to its hydrophobicity, the solubilized molecules will not leak significantly from the aggregates upon storage.
5. The size of aggregates is very small, 300–1000 Å in diameter, and it is expected to cause less problems upon in vivo administration compared to particles, liposomes etc. The size may be controlled by proper use of modification agents.
6. The chemical modification of the antibodies is very simple, and is performed in such a way that the biological activity and antigen recognition are not affected.
7. The same process may be applied to other biologically active substances which have a recognition capability.
8. The same process may be applied even without modification of the antibody, by the use of specific molecules such as protein A.
9. The same process may be applied by physical attachment of hydrophobic groups to the antibody without covalent binding.

FORMATION OF SURFACE ACTIVE ANTIBODIES a. The first stage is based on formation of active esters of fatty acids. These esters were synthesized by a reaction of various fatty acids and N-hydroxysuccinimide in the presence of dicyclocarbodiimide, as shown in eq. 1. Esters having hydrophobic groups between $C_8$–$C_{18}$ were synthesized.

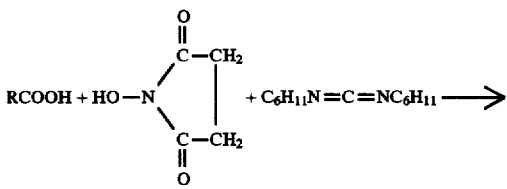

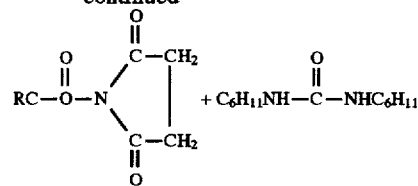

b. The second stage is based on the attachment of the hydrophobic antibody according to equation 2.

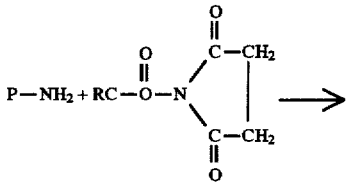

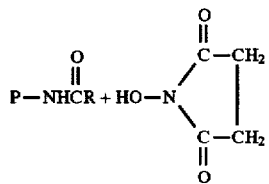

c. For example, attachment of $C_8$ groups is achieved by the following procedure:

c1. IgG solutions in PBS buffer (pH=10) were prepared to final concentration of 6.5 mg/ml. Each solution contained 2% w/w Na-deoxycholate and 0.1% w/w sodium azide.

c2. 0.25 ml solution of N-capryloyl succinimide in dioxan (39 mg/ml) was added dropwise to the IgG solution.

c3. The solution was kept at 25° C. for three hours and then filtered by 0.45 and 0.2 μm Millipore® filters. The solution was dialyzed against phosphate buffer, pH=8.0, for 72 hours with six changes of buffer. The final dialysis is performed against PBS buffer.

c4. Degree of attachment is determined by reaction with TNBS. For the above example, 8 hydrophobic groups are attached to each IgG molecule.

The presence of aggregates is evaluated by classical light scattering, transmission electron microscopy and chromatography on Sepharose®-4b column.

For this specific example, the average aggregation number is 6.8. However, it was found that either increasing the chain length of the groups or an increase in the number of the attached groups lead to an increase in aggregation number. A typical electron microscope picture of such aggregates is presented in FIG. 2.

EXAMPLE 1

Various aggregates were formed by the above method in which various numbers of hydrophobic groups were attached to the antibody molecule.

The ability of these aggregates to solubilize hydrophobic markers was tested on Sudan III and a fluorescent dye 5-(N-octadecanol) aminofluorescein.

As shown in FIG. 3, the aggregates can indeed solubilize the hydrophobic dye, while increasing the chain length of the hydrophobic group leads to an increase in solubilization ratio.

EXAMPLE 2

Since attachment of hydrophobic groups may lead to loss of biological activity, the optimal chain length and degree of modification were evaluated by Elisa measurement. It was concluded that low degree of modification and short chain length ($C_8$) leads to formation of antibodies which retain their biological activity, as presented in FIG. 4. A higher degree of modification decreases the biological activity, probably because of denaturation of the IgG molecules.

After the optimal conditions for obtaining aggregates which are capable of solubilizing hydrophobic markers and still retain their recognition ability were determined, in vitro experiments were performed. The treated antibody preparations were evaluated to the specific antigenic recognition using the immunofluorescent technique in 2 cell lines.

(1) BCS-1 (derived from green monkeys kidney)

(2) Daudi cells (originated from human Burkitt lymphoma).

The tested modified samples were adsorbed on either normal non-infected (control) cells, or onto cells infected with HSV-1. Following 30 min. incubation in 37° C., 5% $CO_2$ atmosphere, the cells were rinsed, FITC labelled anti-human γ chain serum was added and the cells were further incubated for an additional 45 min.

Screening under the fluorescent microscope clearly demonstrated that staining was specific—that is: normal non-infected cells were not stained whatsoever. HSV infected cells were highly positive. Level of recognition (titer of the preparations as compared to native samples) was found to be dependent on the percentage of transformation.

After concluding that the modified antibodies do retain their recognition ability, experiments were conducted to determine if the aggregates can be attached to specific antigens.

As demonstrated by in vitro experiments, the aggregates are indeed targeted to specific cells. A hydrophobic fluorescent dye was solubilized in a solution which contained aggregates of antibodies which have high titer value for Herpes Simplex virus 1 (HSV-1). When the solution was mixed for a short period of time with Herpes-infected cells (BSC-1), it was found that all the cells were stained by the fluorescent dye. Control experiments performed either on native cells (not infected by HSV), or without antibodies or with only native antibodies gave negative results. Therefore it can be concluded that the suggested new method is capable of targeting hydrophobic molecules to specific cells. This clearly indicates that various hydrophobic drugs which might be incorporated into the antibody-aggregates might be targeted to specific sites in the body. Moreover, these aggregates can be used for diagnostic purposes, while the solubilized molecules are chosen in a way which will allow rapid detection of signals, only when the aggregates are bound to specific antigens.

The attached drawings represent:

BRIEF DESCRIPTION OF THE DRAWINGS

FIG. 3 a graph showing the solubilization of Sudan III in various types of aggregates.

Figure 1:
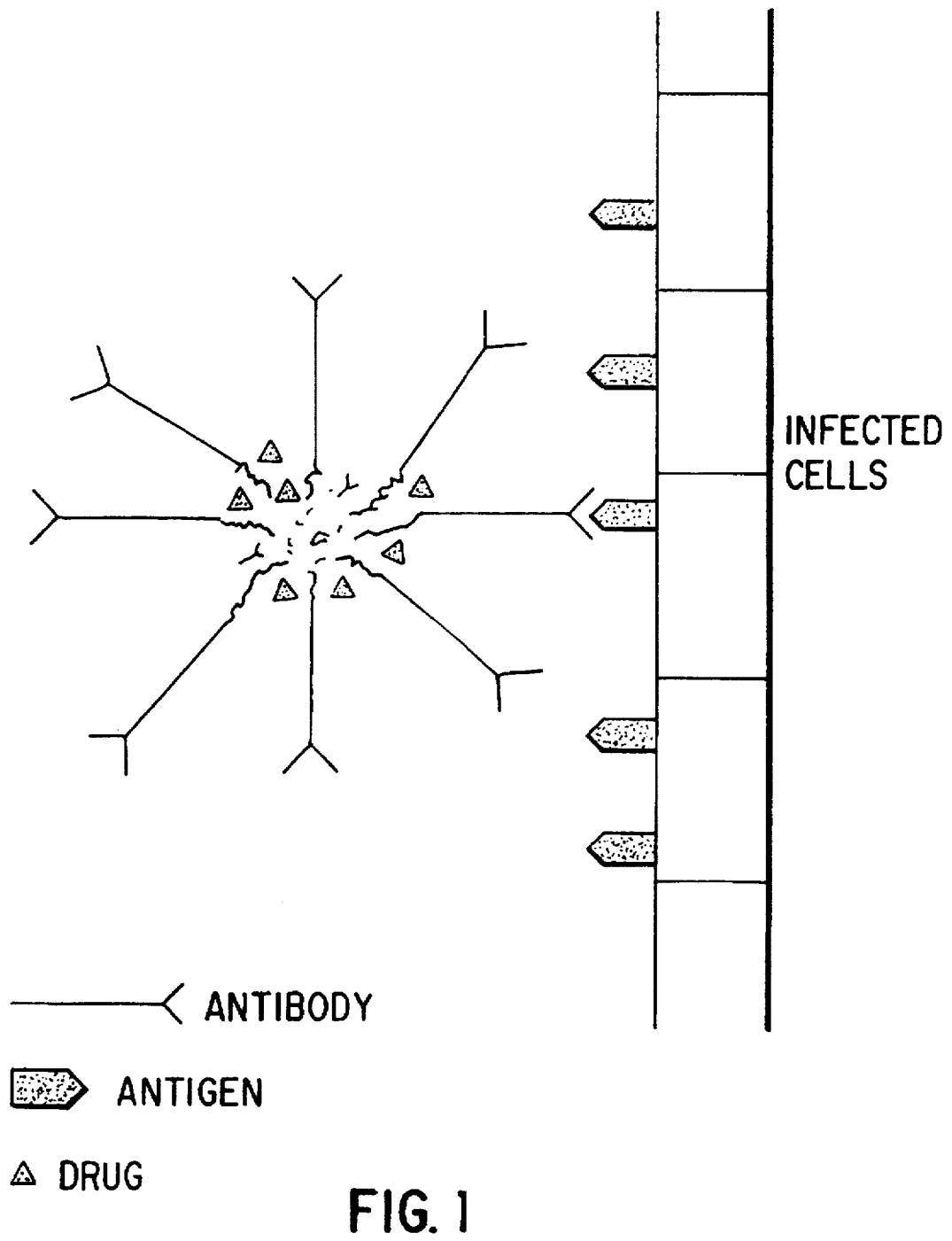
FIG. 1 a schematic representation of the attachment of antibodies to cells which present antigens on their surface.
Figure 2:
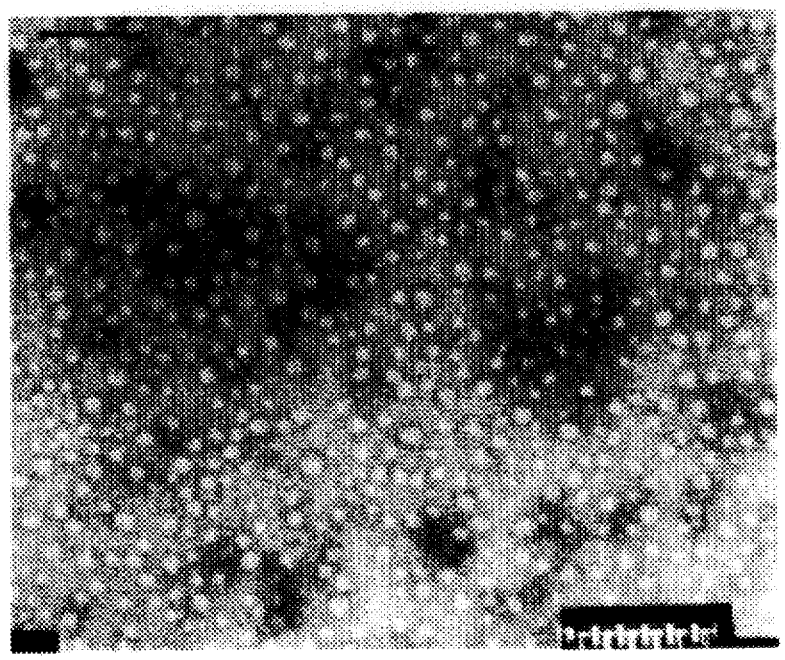
FIG. 2 a transmission electron micrograph of C-8 [correctly C18] aggregates.

We claim:

1. A pharmaceutical or diagnostic composition comprising 1) micelle-like antibody aggregates that are formed from antibodies having hydrophobic chains, wherein said micelle-like antibody aggregates are produced by a process comprising attaching hydrophobic chains to antibodies in the presence of a surface-active agent, removing said surface-active agent, and allowing said antibodies with attached hydrophobic chains to form micelle-like antibody aggregates in an aqueous medium, and 2) pharmaceutically active or diagnostically useful hydrophobic molecules which are solubilized by the hydrophobic chains of the derivatized antibodies within the micelle-like antibody aggregate.

2. The pharmaceutical composition according to claim 1 wherein said micelle-like antibody aggregates are about 20 to 100 nm in diameter.

3. The pharmaceutical or diagnostic composition according to claim 1 wherein said pharmaceutically active or diagnostically useful molecules are chemically modified and made hydrophobic.

4. The pharmaceutical composition according to claim 1 wherein said pharmaceutically active molecules are useful for cancer chemotherapy, inflammations, or infectious diseases including fungi or viral infections.

5. The diagnostic composition according to claim 1 wherein said diagnostically useful molecules are detectable by suitable instruments and said composition is useful for cancer diagnosis.

6. The diagnostic composition according to claim 1 wherein said diagnostically useful molecules are detectable by suitable instruments and said composition is useful for in vitro diagnosis.

7. A process for the preparation of the pharmaceutical or diagnostic composition according to claim 1 comprising:

a) attaching hydrophobic chains to antibodies in the presence of a surface-active agent, removing the surface-active agent, and allowing the antibodies with attached hydrophobic chains to form micelle-like antibody aggregates in an aqueous medium; and b) solubilizing hydrophobic drugs or marker molecules in said micelle-like antibody aggregates.

8. The process for the preparation of a pharmaceutical or diagnostic composition according to claim 7 wherein attaching hydrophobic chains to antibodies of step a) is performed by:

i) forming active esters of fatty acids and ii) coupling said active esters of fatty acids to said antibodies.

9. The process according to claim 8 wherein the active esters of fatty acids are synthesized by a reaction of fatty acids and N-hydroxysuccinimide or derivatives of N-hydroxysuccinimide in the presence of dicyclocarbodiimide.

10. The process according to claim 7 wherein the attachment of the hydrophobic chains to the antibodies is a covalent attachment.

* * * * *